United States Patent [19]
Hohmann et al.

[11] Patent Number: 5,017,725
[45] Date of Patent: May 21, 1991

[54] PREPARATION OF ADDITION SALTS OF CYSTEAMINE WITH ACIDS

[75] Inventors: Andreas Hohmann, Ludwigshafen; Wolfgang Reuther, Heidelberg; Rolf Fikentscher, Ludwigshafen; Theo Proll, Bad Durkheim, all of Fed. Rep. of Germany

[73] Assignee: BASF Aktiengesellschaft, Ludwigshafen, Fed. Rep. of Germany

[21] Appl. No.: 471,080

[22] Filed: Jan. 30, 1990

Related U.S. Application Data

[63] Continuation of Ser. No. 283,129, Dec. 12, 1988, abandoned.

[30] Foreign Application Priority Data

Dec. 12, 1987 [DE] Fed. Rep. of Germany ....... 3742265

[51] Int. Cl.$^5$ ............................................ C07C 323/25
[52] U.S. Cl. .................... 564/487; 548/146; 548/147; 564/1; 564/462; 564/500
[58] Field of Search .................. 564/487, 500, 1, 462; 548/146, 147

[56] References Cited

U.S. PATENT DOCUMENTS 3,574,698  4/1971  Brois et al. ...................... 564/500 X
4,374,247  2/1983  Osawa et al. ........................ 548/146
4,507,500  3/1985  Nakayama et al. .............. 564/487 X
4,584,407  4/1986  Hollowood .......................... 564/487

FOREIGN PATENT DOCUMENTS 747733  10/1944  Fed. Rep. of Germany .
3025461   1/1981  Fed. Rep. of Germany .
39-414    6/1973  Japan .

OTHER PUBLICATIONS

Chemical Abstracts, Band 79, Nr. 19, Nov. 12, 1973, Seite 354, Nr. 125805d, Columbus, Ohio.
Ann. Chem., vol. 566, pp. 210 et seq., 1950.

Primary Examiner—Richard L. Raymond
Attorney, Agent, or Firm—Oblon, Spivak, McClelland, Maier & Neustadt

[57] ABSTRACT

Addition salts of cysteamine with acids are prepared by reacting aziridine with an organic sulfur compound of oxidation state $-2$ and with a ketone and then subjecting the thiazolidine formed as an intermediate to acid hydrolysis, by a process in which aziridine and the ketone are reacted with ammonium hydrogen sulfide or with a metal hydrogen sulfide with the addition of a moderately strong or strong acid at from $-10°$ to $+100°$ C. and a pH which is greater than or equal to 8.5 is maintained.

3 Claims, No Drawings

PREPARATION OF ADDITION SALTS OF CYSTEAMINE WITH ACIDS

This application is a continuation of application Ser. No. 283,129, filed on Dec. 12, 1988, now abandoned.

The present invention relates to a novel process for the preparation of addition salts of cysteamine with acids by reacting aziridine with an inorganic sulfur compound of oxidation state −2 and with a ketone and then subjecting the thiazolidine formed as an intermediate to acid hydrolysis, wherein aziridine and the ketone are reacted with ammonium hydrogen sulfide or with a metal hydrogen sulfide, with the addition of a moderately strong or strong acid, at a pH greater than or equal to 8.5.

DE-A-3 025 461 discloses that 2-aminoethyl hydrogen sulfate can be reacted with a ketone to give a thiazolidine derivative and the latter can then be converted by acid hydrolysis into an addition salt of cysteamine with acids. However, this process is very expensive since thiazolidine formation has to be carried out partly in an autoclave, and the resulting thiazolidine, after it has been worked up, must always be purified by distillation. Moreover, the half ester of 2-aminoethanol with sulfuric acid has to be prepared in an additional intermediate stage.

JP-A-39 414/1973 describes the reaction of aziridine with a ketone and hydrogen sulfide to give a thiazolidine derivative, which is then converted by acid hydrolysis into an addition salt of cysteamine with an acid. The synthesis route described there for the thiazolidine derivative is also disclosed in Ann. Chem. 566 (1950), 210 et seq., and in DE-A-747 733. The disadvantage of this process lies in the use of hydrogen sulfide, which is highly toxic and therefore necessitates expensive safety measures when it is used.

It is an object of the present invention to provide a novel process for the preparation of addition salts of cysteamine with acids, which can be carried out in a simple manner and without expensive apparatus or safety measures.

We have found that this object is achieved and that the preparation of addition salts of cysteamine with acids by reacting aziridine with an inorganic sulfur compound of oxidation state −2 and with a ketone of the formula I

where $R^1$ and $R^2$ are identical or different and independently of one another are each $C_1$-$C_6$-alkyl, or $R^1$ and $R^2$ together form $C_4$-$C_6$-alkylene, and then subjecting the thiazolidine of the formula II

where $R^1$ and $R^2$ each have the abovementioned meanings, which is formed as an intermediate, to hydrolysis in the presence of an acid can be carried out in an advantageous manner if aziridine and the ketone of the formula I are reacted with ammonium hydrogen sulfide or with a metal hydrogen sulfide with the addition of a moderately strong or strong acid at from −10° to +100° C. and a pH which is greater than or equal to 8.5 is maintained.

In formula I, $R^1$ and $R^2$ are each, for example, methyl, ethyl, propyl, isopropyl, butyl, isobutyl, secbutyl, pentyl, isopentyl, neopentyl, tert-pentyl, hexyl or 2-methylpentyl.

Where $R^1$ and $R^2$ together form $C_4$-$C_6$-alkylene, examples of radicals are tetramethylene, pentamethylene, hexamethylene, 2-methyltetramethylene and 2- and 3-methylpentamethylene.

Acetone, methyl ethyl ketone or cyclohexanone is preferably used as the ketone of the formula I.

The metal hydrogen sulfides to be used in the novel process are, for example, alkali metal or alkaline earth metal hydrogen sulfides, such as lithium hydrogen sulfide, sodium hydrogen sulfide, potassium hydrogen sulfide, magnesium hydrogen sulfide or calcium hydrogen sulfide. Ammonium hydrogen sulfide or an alkali metal hydrogen sulfide is preferably used, sodium hydrogen sulfide and potassium hydrogen sulfide being particularly preferred.

It is of course also possible to start from the corresponding sulfides. As a result of the addition, according to the invention, of a moderately strong or strong acid, they are then converted into the particular hydrogen sulfides.

For the purposes of the present invention, moderately strong or strong acids are, as a rule, acids whose $pK_a$ is less than or equal to 3.5. In general, the $pK_a$ is from −10 to +3.5.

According to the invention, both inorganic and organic acids can be used, provided that their $pK_a$ meets the abovementioned requirement.

Examples of such acids are hydrochloric acid, hydrobromic acid, hydrofluoric acid, sulfuric acid, nitric acid, phosphoric acid, trifluoroacetic acid, trichloroacetic acid, methanesulfonic acid, benzenesulfonic acid and p-toluenesulfonic acid.

A strong inorganic acid is preferably used, hydrochloric acid being particularly preferred.

The novel process, which can be carried out by a continuous or batchwise procedure, is advantageously effected by initially taking the ketone I and the particular hydrogen sulfide, which is advantageously used in the form of a 10–70% strength aqueous solution, and adding aziridine and the moderately strong or strong acid to this mixture. The aziridine and the acid can be added at different times, i.e. First the aziridine and then the acid, or, preferably, simultaneously but at separate points from one another. It is also possible to add aziridine and acid alternately a little at a time.

The reaction is preferably carried out under atmospheric pressure or slightly superatmospheric pressure (up to about 2 bar) and can be effected in the presence or absence of a protective gas. It is preferably carried out in the presence of a protective gas. Examples of suitable protective gases are nitrogen and helium.

It is important to maintain a pH which is greater than or equal to 8.5, preferably from 9 to 12, during the reaction.

In general, from 0.5 to 1.5 moles of aziridine, from 0.5 to 1.5 equivalents of hydrogen sulfide and from 0.5 to 1.5 equivalents of acid are required per mole of ketone.

The time required for the addition of aziridine and acid is in general from 0.5 to 5, preferably from 1 to 2, hours. The reaction temperature is from −10° to +100°

C., preferably from 0° to 60° C., in particular from 20° to 40° C.

After a further stirring phase of 0.5–4 hours, which is effected in the abovementioned temperature range, the resulting organic phase, which contains the thiazolidine II, is separated from the aqueous phase and acid is added for the purpose of hydrolysis.

An advantageous acid in this case is the acid added in the reaction of the aziridine. However, it is also possible to use another acid for hydrolysis. The choice of the acid in this case depends primarily on the particular addition salt of cysteamine and acid which is finally desired. The use of hydrochloric acid is also preferred here.

As a rule, from 1 to 1.2, preferably from 1.05 to 1.2, equivalents of acid are added per equivalent of basic nitrogen in the organic phase, and the reaction mixture is heated to the boil (about 70°–110° C.), the thiazolidine II being hydrolyzed and the ketone I formed in the hydrolysis distilling off.

After a reaction time of from 0.5 to 4 hours, the hydrolysis is complete. The resulting solution of the addition salt of cysteamine with the acid is cooled and requires no further purification. It is then possible to free the cysteamine salt from the water or even to use it directly in solution. In some cases, it may also be advantageous to treat the aqueous solution of the said salt with active carbon.

Cysteamine hydrochloride is a useful intermediate for the preparation of the $H_2$ blockers cimetidine and ranitidine.

The Examples which follow illustrate the invention.

EXAMPLE 1

420 g (3.0 moles) of 40% strength by weight aqueous sodium hydrogen sulfide solution and 238 g (3.3 moles) of ethyl methyl ketone were initially taken under nitrogen. 215 g (3.0 moles) of 60% strength by weight aqueous aziridine and 365 g (3.0 moles) of 30% strength by weight hydrochloric acid were added dropwise to the stirred mixture, simultaneously and continuously in the course of 1.5 hours, from separate feed vessels, the pH not falling below 8.5. The reaction temperature was from 30° to 40° C. When the addition was complete, stirring was continued for 1 hour at 50° C.

The lower (aqueous) phase was separated off, and 989 g (2.7 moles) of 10% strength by weight hydrochloric acid were added to the upper (thiazolidine-containing) phase (390 g, 2.48 equivalents of basic nitrogen = 83% yield, based on aziridine). The solution was heated and ethyl methyl ketone/water was distilled off up to a distillation temperature of 100° C. The clear reaction solution was evaporated down, and 279 g (2.46 moles = 82% of theory) of colorless cysteamine hydrochloride of melting point 63°–67° C. were isolated.

$C_2H_8NSCl$ Calc.: C=21.2 H=7.0 N=12.3 S=28.2 Cl=31.3
113.61 Found: C=21.2 H=7.0 N=12.3 S=27.2 Cl=31.3

SH content (iodometric determination): 8.84 mmol/g (100% of theory)

Recrystallization from isopropanol gave cysteamine hydrochloride of melting point 63°–68° C.

EXAMPLE 2

336 g (3.0 moles) of 50% strength by weight aqueous sodium hydrogen sulfide solution and 238 g (3.3 moles) of ethyl methyl ketone were initially taken under nitrogen, and the mixture was brought to pH 9 with 20% strength by weight hydrochloric acid. 129 g (3.0 moles) of aziridine were added dropwise to the mixture. The pH was kept at 8.9–9.1 with 20% strength by weight hydrochloric acid. The internal temperature was 30°–40° C. When the addition was complete, the mixture was refluxed for 1 hour, cooled to 25° C. and brought to pH 8.5 with hydrochloric acid, and the lower phase was separated off. The total consumption of 20% strength by weight hydrochloric acid was 594 g (3.3 moles).

913 g (2.5 moles) of 10% strength by weight hydrochloric acid were added to the thiazolidine-containing upper phase (375 g, 2.26 equivalents of basic nitrogen = 75% yield, based on aziridine), the liberated ethyl methyl ketone was distilled off, the crude product solution was filtered over 20 g of active carbon and the filtrate was evaporated down.

Yield of cysteamine hydrochloride: 222 g (1.95 moles = 65% of theory)

mp.: 60°–68° C. (recrystallized from isopropanol: 62°–67° C.)

$C_2H_8NSCl$ Calc.: C=21.1 H=7.0 N=12.3 S=28.2 Cl=31.3
113.61 Found: C=20.8 H=6.6 N=12.1 S=26.8 Cl=31.8

SH content (iodometric determination): 8.84 mmol/g (100% of theory)

EXAMPLE 3

The reaction with cyclohexanone as the ketone was carried out similarly to Example 2.

Consumption of 20% strength by weight hydrochloric acid during the reaction: 550 g (3.0 moles).

Thiazolidine-containing phase: 510 g (2.66 equivalents of basic nitrogen = 89% yield, based on aziridine).

Hydrolysis of thiazolidine was effected by the addition of 1070 g (2.9 moles) of 10% strength by weight hydrochloric acid followed by azeotropic distillation of the cyclohexanone. The crude product solution was filtered twice over active carbon.

Yield of cysteamine hydrochloride: 261 g (2.29 moles = 77% of theory)

mp.: 63°–66° C. (recrystallization from isopropanol: 60°–67° C.)

$C_2H_8NSCl$ Calc.: C=21.1 H=7.0 N=12.3 S=28.2 Cl=31.3
113.61 Found: C=21.0 H=7.1 N=12.0 S=26.5 Cl=32.5

SH content (iodometric determination): 8.70 mmol/g (99% of theory)

EXAMPLE 4

The reaction with acetone as the ketone was carried out similarly to Example 2.

Consumption of 20% strength by weight hydrochloric acid during the reaction: 662 g (3.6 moles)

Thiazolidine-containing phase: 237 g (1.52 equivalents of basic nitrogen = 51% yield, based on aziridine).

After the addition of 603 g (1.7 moles) of 10% strength by weight hydrochloric acid, working up was carried out as in Example 2.

Yield of cysteamine hydrochloride: 161.3 g (1.42 moles = 47% of theory).

mp.: 55°–63° C. (recrystallization from isopropanol: 55°–67° C.)

$C_2H_8NSCl$ Calc.: C=21.1 H=7.0 N=12.3 S=28.2 Cl=31.3

113.61 Found: C=22.5 H=7.4 N=11.7 S=26.2 Cl=30.7

SH content (iodometric determination): 8.07 mmol/g (92% of theory).

We claim:

1. A process for the preparation of an addition salt of cysteamine with an acid by reacting aziridine with an inorganic sulfur compound of oxidation state −2 and with a ketone of the formula I

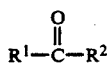  (I)

where $R^1$ and $R^2$ are identical or different and independently of one another are each $C_1$-$C_6$-alkyl, or $R^1$ and $R^2$ together form $C_4$-$C_6$-alkylene, and then subjecting the thiazolidine of the formula II

  (II)

where $R^1$ and $R^2$ each have the abovementioned meanings, which is formed as an intermediate, to hydrolysis in the presence of an acid, wherein aziridine and the ketone of the formula I are reacted with ammonium hydrogen sulfide or with a metal hydrogen sulfide with the addition of a moderately strong or strong acid at from −10° to +100° C. and a pH which is greater than or equal to 8.5 is maintained.

2. A process as claimed in claim 1, wherein the reaction of aziridine is carried out with the addition of a strong inorganic acid.

3. A process as claimed in claim 1, wherein the reaction of aziridine is carried out with the addition of hydrochloric acid.

* * * * *